United States Patent [19]
Edwards

[11] Patent Number: 5,827,277
[45] Date of Patent: Oct. 27, 1998

[54] MINIMALLY INVASIVE APPARATUS FOR INTERNAL ABLATION OF TURBINATES

[75] Inventor: Stuart D. Edwards, Portola Valley, Calif.

[73] Assignee: Somnus Medical Technologies, Inc., Sunnyvale, Calif.

[21] Appl. No.: 790,081

[22] Filed: Jan. 29, 1997

Related U.S. Application Data

[63] Continuation-in-part of Ser. No. 754,588, Oct. 19, 1996, and a continuation-in-part of Ser. No. 753,063, Oct. 19, 1996, and a continuation-in-part of Ser. No. 752,076, Oct. 19, 1996, which is a continuation-in-part of Ser. No. 651,796, May 22, 1996, which is a continuation-in-part of Ser. No. 651,798, May 22, 1996, abandoned, which is a continuation-in-part of Ser. No. 265,459, Jun. 24, 1995, Pat. No. 5,505,730.

[51] Int. Cl.[6] ........................................ A61B 17/39
[52] U.S. Cl. ............................ 606/41; 606/48; 607/101; 607/102
[58] Field of Search ............................ 606/41, 42, 45, 606/50, 15, 16; 607/100–102, 122, 123; 128/642; 600/372–374

[56] References Cited

U.S. PATENT DOCUMENTS 3,933,157  1/1976  Bjurwill et al. .
3,990,452  11/1976 Murry et al. .
4,011,872  3/1977  Komiya .

(List continued on next page.)

FOREIGN PATENT DOCUMENTS

92/10142    6/1992   WIPO .
WO 92/10142 6/1992   WIPO .
WO 96/29946 10/1996  WIPO .

OTHER PUBLICATIONS

Joseph C. Beck, M.D., "Annals of Otology, Rhinology and Laryngology", Incorporating the Index of Othalaryngology, vol. 39, pp. 349–363, (1930).

N.P. Warnick–Brown, et al., "Turbinate Surgery: How Effective is it?", A Long–Term Assessment, ORL 49:, pp. 314–320, (1987).

G. Brun, et al., "Endometrial Resection For Metorrhagla" 45 Case Histories.

J.A. Cook, "Laser Treatment of Rhinitis" One Year Follow Up, Clin. Otolaryngol, pp. 209–211, (1993).

(List continued on next page.)

Primary Examiner—Michael Peffley
Attorney, Agent, or Firm—Wilson Sonsini Godrich & Rosati

[57] ABSTRACT

A method and apparatus for ablating at least a portion of a nasal concha. The apparatus includes a catheter having a distal portion with a dimension configured for positioning through a nostril of a patient into a nasal meatus adjacent a nasal concha, and an energy delivery device coupled to the catheter distal portion including one or more energy delivering probes extendable from the catheter distal portion a sufficient distance to be inserted into an interior of the nasal concha to deliver ablative energy therein. The distal portion of the apparatus may also include an expandable member, expansion of the expandable member within the nasal meatus immobilizing the distal portion within the nasal meatus.

26 Claims, 13 Drawing Sheets

U.S. PATENT DOCUMENTS

| | | |
|---|---|---|
| 4,411,266 | 10/1983 | Cosman . |
| 4,476,862 | 10/1984 | Pao . |
| 4,532,924 | 8/1985 | Auth et al. . |
| 4,565,200 | 1/1986 | Cosman . |
| 4,674,499 | 6/1987 | Pao . |
| 4,907,589 | 3/1990 | Cosman . |
| 4,947,842 | 8/1990 | Marchosky et al. . |
| 4,966,597 | 10/1990 | Cosman . |
| 4,976,711 | 12/1990 | Parins et al. . |
| 5,057,107 | 10/1991 | Parins et al. . |
| 5,078,717 | 1/1992 | Parins et al. . |
| 5,083,565 | 1/1992 | Parins . |
| 5,100,423 | 3/1992 | Fearnot . |
| 5,122,137 | 6/1992 | Lennox . |
| 5,125,928 | 6/1992 | Parins et al. . |
| 5,190,541 | 3/1993 | Abele et al. . |
| 5,197,963 | 3/1993 | Parins . |
| 5,197,964 | 3/1993 | Parins . |
| 5,215,103 | 6/1993 | Desai . |
| 5,257,451 | 11/1993 | Edwards et al. . |
| 5,275,162 | 1/1994 | Edwards et a . |
| 5,281,217 | 1/1994 | Edwards et al. . |
| 5,281,218 | 1/1994 | Imran . |
| 5,290,286 | 3/1994 | Parins . |
| 5,293,869 | 3/1994 | Edwards et al. . |
| 5,309,910 | 5/1994 | Edwards et al. . |
| 5,313,943 | 5/1994 | Houser et al. . |
| 5,314,466 | 5/1994 | Stern et al. . |
| 5,328,467 | 7/1994 | Edwards et al. . |
| 5,348,554 | 9/1994 | Imran et al. . |
| 5,363,861 | 11/1994 | Edwards et al. . |
| 5,365,926 | 11/1994 | Desai . |
| 5,366,490 | 11/1994 | Edwards et al. . |
| 5,368,592 | 11/1994 | Stern et al. . |
| 5,370,675 | 12/1994 | Edwards et al. ........................ 607/101 |
| 5,370,678 | 12/1994 | Edwards et al. . |
| 5,383,876 | 1/1995 | Nardella . |
| 5,383,917 | 1/1995 | Desai . |
| 5,385,544 | 1/1995 | Edwards et al. . |
| 5,397,339 | 3/1995 | Desai . |
| 5,398,683 | 3/1995 | Edwards et al. . |
| 5,403,311 | 4/1995 | Abele et al. ........................... 606/49 |
| 5,409,453 | 4/1995 | Lundquist et al. . |
| 5,421,819 | 6/1995 | Edwards et al. . |
| 5,423,808 | 6/1995 | Edwards et al. . |
| 5,423,811 | 6/1995 | Imran et al. . |
| 5,433,739 | 7/1995 | Sluijter et al. . |
| 5,435,805 | 7/1995 | Edwards et al. . |
| 5,456,662 | 10/1995 | Edwards et al. . |
| 5,456,682 | 10/1995 | Edwards et al. . |
| 5,458,596 | 10/1995 | Lax et al. . |
| 5,458,597 | 10/1995 | Edwards et al. . |
| 5,470,308 | 11/1995 | Edwards et al. . |
| 5,471,982 | 12/1995 | Edwards et al. . |
| 5,472,441 | 12/1995 | Edwards et al. . |
| 5,484,400 | 1/1996 | Edwards et al. . |
| 5,486,161 | 1/1996 | Lax et al. . |
| 5,500,012 | 3/1996 | Brucker et al. ........................ 607/122 |
| 5,505,730 | 4/1996 | Edwards . |
| 5,507,743 | 4/1996 | Edwards et al. . |
| 5,509,419 | 4/1996 | Edwards et al. . |
| 5,514,130 | 5/1996 | Baker . |
| 5,514,131 | 5/1996 | Edwards et al. . |
| 5,520,684 | 5/1996 | Imran . |
| 5,531,676 | 7/1996 | Edwards et al. . |
| 5,531,677 | 7/1996 | Lundquist et al. . |
| 5,536,240 | 7/1996 | Edwards et al. . |
| 5,536,267 | 7/1996 | Edwards et al. . |
| 5,540,655 | 7/1996 | Edwards et al. . |
| 5,542,915 | 8/1996 | Edwards et al. . |
| 5,542,916 | 8/1996 | Hirsch et al. . |
| 5,545,161 | 8/1996 | Imran . |
| 5,545,171 | 8/1996 | Sharkey et al. . |
| 5,545,193 | 8/1996 | Fleischman et al. . |
| 5,549,108 | 8/1996 | Edwards et al. . |
| 5,549,644 | 8/1996 | Lundquist et al. . |
| 5,554,110 | 9/1996 | Edwards et al. . |
| 5,556,377 | 9/1996 | Rosen et al. . |
| 5,558,672 | 9/1996 | Edwards et al. . |
| 5,558,673 | 9/1996 | Edwards et al. . |
| 5,571,154 | 11/1996 | Ren . |
| 5,672,173 | 9/1997 | Gough et al. ........................... 606/41 |

OTHER PUBLICATIONS

Baldev K. Devgan, M.D., et al. "Submuscosal Diathermy of Inferior Turbinates", vol. 55, pp. 156–159, (1976).

Carol L. Wengraf, et al., "The Stuffy Nose" A Comparative Study of Two Common Methods of Treatment, Clin. Otolaryngol, 11, pp. 61–68, (1986).

A. Granapragsam, "Therapeutic Effects of Sub–Mucous Diathermy of Inferior Tubinates, with Special Reference To Ethnic Groups in Malaya", The Medical Journal of Malaya, vol. 26, No. 4, (1972).

Henry Horn, M.D., "The Treatment of Intumscent Rhintis by a Submucous Method", pp. 490–495.

Lee M. Hurd, "Biopolar Electrode For Electrocoagulation of the Inferior Turbinate", Archives of Otolaryngology, p. 442, (1930).

A.S. Jones, et al., "Does Submucosal Diathermy to the Inferior Turbinates Reduce Nasal Resistance to Airflow in the Long Term?", The Jourrnal of Laryngology and Otology, vol. 10 101, pp. 448–451, (1987).

A.S. Jones, et al., "The Effect of Submucosal Diathermy to the Inferior Turbinates on Nasal Resistance to Airflow in Allergic and Vasomotor Rhinitis", Clin. Otolaryngol., 10, pp. 249–252 (1985).

A.S. Jones, et al., "Predicting the Outcome of Submucosal Diatherymy to the Inferior Turbinates", Clin. Otolaryngol, pp. 41–44, (1989).

Martin Jourdan, et al, "Diathermy and Cautery Equipment", British Journal of Hospital Medicine, pp. 89–92, (1981).

A.W. McCombe, et al, "A Comparison of Laser Cautery and Sub–Mucosal Diatherymy for Rhinitis", Clin. Otolaryngol, 17, pp. 297–299, (1992).

J.R.M. Moore, et al., "A Comparison of Cyrosurgery and Submucous Diatherymy in Vasomotor Rhinitis", The Journal of Laryngology and Otology, vol. 94, pp. 1411–1413, (1980).

N. Murata, et al., Submucosal Dissection of the Esophagus: A Case Report, Endoscopy, vol. 23, pp. 95–97, (1991).

Dr. Franz Nagelschmidt, F (1909) Munchener Medizinishe Wochenschrift, 56 2575.

F.E. Neres, M.D., "Voltaic Turbinal Puncture For the Relief of Intumescent and Hypertrophic Rhinitis" Jour. A.M.A., vol. 69, (1907).

H. Lenders, et al., "How Can Vasomotor Rhinitis Be Influenced Surgically?", Laryngo–Rhino–Otol. vol. 69, pp. 246–254, 1990.

D.J. Premachandra F.R.C.S., et al., "How Safe is Submucosal Diathermy?", The Journal of Laryngology and Otology, vol. 104, pp. 408–409, (1990).

John R. Richardson, M.D., "Turbinate Treatment in Vasomotor Rhinitis", pp. 834–847.

T. Sauerbruch,et al., "Lymphangioma of the Duodenum", Endocscopy, vol. 9, pp. 179–182, (1977).

Lee Shahinian, M.D., "Chronic Vasomotor Rhinitis", A.M.A. Archives of Otolaryngology, vol. 57, No. 5, pp. 475–489, (1953).

J.F. Simpson et al., "Submucosal Diathermy of the Inferior Turbinates", pp. 292–301.

Maddough Talaat, et al., "Submucous Diathermy of the Interior Turbinates in Chronic Hypertrophic Rhinitis", The Journal of Layngology and Otology, vol. 101, pp. 542–460, (1987).

H.O. Williams, F.R.C.S., et al., "Two Stage Turbinectomy: Sequestration of the Inferior Turbinate Following Submucosal Diathermy", The Journal of Laryngology and Otology, vol. 105, pp. 14–16, (1991).

Norman P. Von Haacke, et al., "Submucosal Dithermy of the Inferior Tubinate and the Congested Nose.", ORL 47, pp. 189–193, (1985).

C.J. Woodhead, F.R.C.S., et al., "Some Observations on Submucous Diathermy", The Journal of Laryngology and Otology, vol. 103, pp. 1047–1049, (1989).

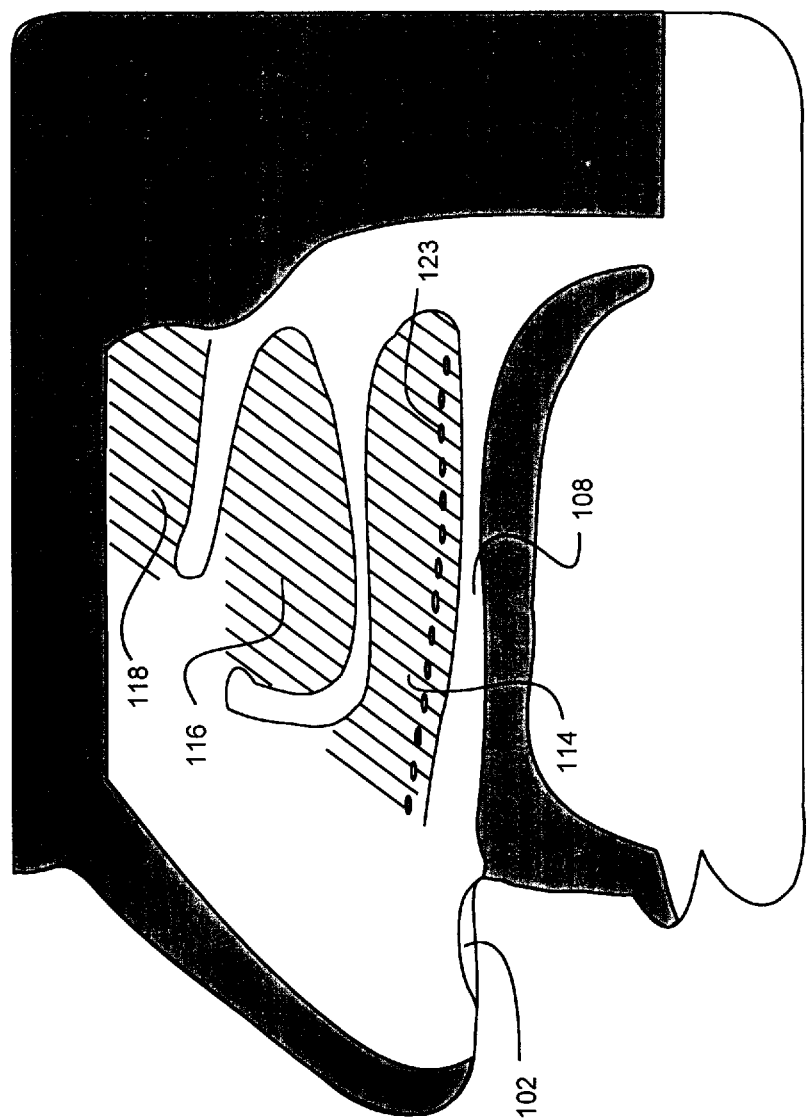

MINIMALLY INVASIVE APPARATUS FOR INTERNAL ABLATION OF TURBINATES

RELATIONSHIP TO COPENDING APPLICATIONS

This application is a continuation-in-part of application Ser. No. 08/754,588, "Method for Ablating Turbinates", filed Oct. 19, 1996; application Ser. No. 08/753,063, "Apparatus for Ablating Turbinates", filed Oct. 19, 1996 and application Ser. No. 08/752,076, "Noninvasive Apparatus for Ablating Turbinates", filed Oct. 19, 1996 all of which are continuation-in-part applications of application Ser. No. 08/651,796, "Method and Apparatus for Ablating Turbinates" filed May 22, 1996 and of application Ser. No. 08/651,798, "Method and Apparatus for Ablating Turbinates", filed May 22, 1996; all of which are a continuation-in-part of application Ser. No. 08/265,459, now U.S. Pat. No. 5,505,730. "Thin Layer Ablation Apparatus", filed Jun. 24, 1994, all of which are incorporated herein by reference.

FIELD OF THE INVENTION

The present invention relates to a method and apparatus for treating airway obstructions. More specifically, the present invention relates to a method and apparatus for reducing the volume of turbinates in a nasal passageway in order reduce nasal airway obstructions.

BACKGROUND OF THE INVENTION

Sleep-apnea syndrome is a medical condition characterized by daytime hypersomnomulence, morning arm aches, intellectual deterioration, cardiac arrhythmias, snoring and thrashing during sleep. It is caused by frequent episodes of apnea during the patient's sleep. The syndrome is classically subdivided into two types. One type, termed "central sleep apnea syndrome", is characterized by repeated loss of respiratory effort. The second type, termed obstructive sleep apnea syndrome, is characterized by repeated apneic episodes during sleep resulting from obstruction of the patient's upper airway or that portion of the patient's respiratory tract which is cephalad to, and does not include, the larynx.

Treatments for sleep apnea thus far include various medical, surgical and physical measures to unobstruct the airways. Medical measures include the use of medications such as protriptyline, medroxyprogesterone, acetazolamide, theophylline, nicotine and other medications in addition to avoidance of central nervous system depressants such as sedatives or alcohol. The above medical measures are sometimes helpful but are rarely completely effective. Further, the medications frequently have undesirable side effects.

Surgical interventions have included uvulopalatopharyngoplasty, tonsillectomy, surgery to correct severe retrognathia and tracheostomy. Other surgical procedures include pulling the tongue as forward as possible and surgically cutting and removing sections of the tongue and other structures which can close off the upper airway passage. These procedures may be effective but the risk of surgery in these patients can be prohibitive and the procedures are often unacceptable to the patients.

Among the air passageways in the body that can become obstructed are the nasal passageways leading from the nose to the pharynx. There are three nasal passageways, namely the inferior, middle and superior nasal meatus. The turbinates, also referred to as nasal concha, are a series of tissues which form at least a portion of these nasal passageways. Forming a portion of the inferior nasal meatus is the inferior nasal concha. The inferior and middle nasal concha each form a portion of the middle nasal meatus. The middle and superior nasal concha each form a portion of the superior nasal meatus. When the inferior, middle and/or superior nasal concha become enlarged, the various nasal meatus which allow air to pass through the nose into the pharynx can become obstructed.

Opening of obstructed nasal airways by reducing the size of the turbinates has been performed using surgical and pharmaceutical treatments. Examples of surgical procedures include anterior and posterior ethmoidectomy, such as those described in "Endoscopic Paranasal Sinus Surgery" by D. Rice and S. Schaefer, Raven Press, 1988); the writings of M. E. Wigand, Messerklinger and Stamberger; and U.S. Pat. No. 5,094,233. For example, as described in U.S. Pat. No. 5,094,233, the Wigand procedure involves the transection of the middle turbinate, beginning with the posterior aspect, visualization of the sphenoid ostium and opening of the posterior ethmoid cells for subsequent surgery. In the sphenoidectomy step, the ostium of the sphenoid is identified and the anterior wall of the sinus removed. Following this step, the posterior ethmoid cells may be entered at their junction with the sphenoid and the fovea ethmoidalis can be identified as an anatomical landmark for further dissection. In anterior ethmoidectomy, the exenteration of the ethmoids is carried anteriorly to the frontal recess. Complications, such as hemorrhage, infection, perforation of the fovea ethmoidalis or lamina papyracea, and scarring or adhesion of the middle turbinate, are reported in connection with these procedures.

One of the problems encountered as a result of these procedures is postoperative adhesion occurring between the turbinates and adjacent nasal areas, such as medial adhesion to the septum and lateral adhesion to the lateral nasal wall in the area of the ethmoid sinuses. Otherwise successful surgical procedures may have poor results in these cases. Some surgeons have proposed amputation of a portion of the turbinate at the conclusion of surgery to avoid this complication, resulting in protracted morbidity (crust formation and nasal hygiene problems). The turbinate adhesion problem detracts from these endoscopic surgical procedures. Efforts have been made to reduce the complications associated with the surgical treatment of turbinate tissue, for example by the use of a turbinate sheath device. U.S. Pat. No. 5,094,233.

U.S. Pat. No. 3,901,241 teaches a cryosurgical instrument which is said to be useful for shrinking nasal turbinates. U.S. Pat. No. 3,901,241.

Pharmaceuticals have also been developed for reducing the size of the turbinates. However, pharmaceuticals are not always completely efficacious and generally do not provide a permanent reduction in turbinate size. In addition, pharmaceuticals can have adverse side effects.

A need exists for a method and device for clearing obstructed nasal passageways. It is preferred that the method and device be performable with minimal surgical intervention or post operative complications. It is also preferred that the method and device be performable to reduce the size of the turbinates without involving surgical cutting or the physical removal of tissue. It is also preferred that the method and device provide a permanent reduction in turbinate size.

SUMMARY OF THE INVENTION

The present invention relates to a method and apparatus for ablating at least a portion of a nasal concha. In one embodiment, the apparatus includes a catheter having a distal portion with a dimension configured for positioning through a nostril of a patient into a nasal meatus adjacent a nasal concha, and an energy delivery device coupled to the catheter distal portion including one or more energy delivering probes extendable from the catheter distal portion a sufficient distance to be inserted into an interior of the nasal concha to deliver ablative energy therein.

In another embodiment, the apparatus includes a catheter having a distal portion with a dimension configured for positioning through a nostril of a patient into a nasal meatus adjacent a nasal concha, the distal portion including an expandable member, expansion of the expandable member within the nasal meatus immobilizing the distal portion within the nasal meatus, and an energy delivery device coupled to the catheter distal portion including one or more energy delivering probes extendable from the catheter distal portion a sufficient distance to be inserted into an interior of the nasal concha to deliver ablative energy therein.

In this embodiment, the expandable member may be designed to conform to a surface of the nasal concha when expanded and/or to a contour of the nasal meatus. In this embodiment, the apparatus may further include a lumen positioned within the catheter for delivering a medium into the expandable member to expand the expandable member and a medium source for delivering the medium through the lumen into the expandable member.

In another embodiment, the apparatus includes a catheter having a distal portion with a dimension configured for positioning through a nostril of a patient into a nasal meatus adjacent a surface of a nasal concha, an energy delivery device coupled to the catheter distal portion including one or more energy delivering probes extendable from the catheter distal portion a sufficient distance to be inserted into an interior of the nasal concha to deliver ablative energy therein, and an expandable member coupled to the distal portion having a cooling surface, expansion of the expandable member within the nasal meatus placing the cooling surface into contact with a surface of the nasal concha to cool the nasal concha surface.

In this embodiment, the cooling surface preferably provides sufficient cooling to prevent the ablation of the nasal concha surface. The apparatus may further include a lumen positioned within the catheter for delivering a medium into the expandable member to expand the expandable member adjacent the surface of the nasal concha and a medium source for delivering medium of a sufficiently low temperature to cool the surface of the nasal concha. Expansion of the expandable member may also be used to immobilize the catheter distal end within the nasal meatus. In this embodiment, the expandable member may be designed to conform to a surface of the nasal concha when expanded and/or to a contour of the nasal meatus.

In any of the above embodiments, the one or more energy delivering probes may extend a fixed or variable distance from the catheter distal portion. The one or more energy delivering probes are preferably retractable into the catheter distal portion and extendable from the catheter distal portion. At least two energy delivering probes are preferably included in the energy delivery device. An insulator may be used in combination with the probes to control where energy is delivered. In one variation, the insulator is movable relative to the one or more energy delivering probes.

In any of the above embodiments, the energy delivering probes are adapted to deliver one of a variety of forms of ablative energy including, for example, RF, microwave, ultrasonic, pulsed laser and diffuse laser energy. When delivering RF energy, the probes are preferably needle electrodes. When delivering laser energy, the probes are preferably optical fibers. When delivering microwave energy, the probes preferably include microwave antenna. When delivering ultrasonic energy, the probes preferably include ultrasound transducers.

In any of the above embodiments, the apparatus may further include at least one sensor coupled to the processor. The sensor may be used to measure a variety of properties, including an amount of energy delivered by the energy delivery device, an amount of heat generated at a location, an amount of impedance generated, and a temperature at a location. The energy delivered to the energy delivery device may also be controlled by the processor in response to a measured property.

In any of the above embodiments, the apparatus may further include an energy source coupled to the energy delivery device for delivering energy to the probes.

A method is also provided for ablating at least a portion of a nasal concha using a catheter having a distal portion with a dimension configured for positioning through a nostril of a patient into a nasal meatus adjacent a nasal concha and an energy delivery device coupled to the catheter distal portion including one or more energy delivering probes. In the method, the distal portion of the catheter is positioned through a nostril of a patient into a nasal meatus adjacent a surface of a nasal concha. The one or more energy delivering probes are then introduced into an interior of the nasal concha. Sufficient ablative energy is then delivered into the interior of the nasal concha to ablate at least a portion of the nasal concha. In the method, the nasal concha is preferably the inferior nasal concha and the nasal meatus is preferably the inferior nasal meatus. The portion of the nasal concha ablated is preferably an anterior section of the inferior nasal concha. More preferably, less than one-third of the inferior nasal concha in the anterior portion of the inferior nasal concha is ablated. The nasal concha is preferably reduced in size a sufficient amount to increase the rate of airflow through the nasal meatus at a given pressure by at least 25%.

According to the method, ablation of the nasal concha is preferably done without ablating the surface of the nasal concha. Prevention of the surface tissue of the nasal concha from being ablated can be performed by the step of cooling the surface of the nasal concha during the delivery of energy.

In one variation of this method, the catheter includes an expandable member coupled to the catheter distal portion. According to this variation, the method further includes the step of expanding the expandable member within the nasal meatus to immobilize the distal portion within the nasal meatus. Expansion of the expandable member may be performed by delivering a medium into the expandable member which may be delivered through a lumen within the catheter into the expandable member. This medium may also be used in the method to cool the surface of the nasal concha during the delivery of energy in order to prevent the surface of the nasal concha from being ablating.

By using the energy delivering probes, delivery of ablative energy can be performed substantially bloodlessly. In addition, by allowing the ablated tissue to be removed by natural absorption, the step of removing the ablated nasal concha tissue is performed substantially bloodlessly and without introducing an element into the nasal concha.

BRIEF DESCRIPTION OF THE DRAWINGS

FIG. 2 illustrates the effect enlargement of a nasal concha has on a nasal air passageway.

FIG. 3A illustrates the introduction of an apparatus through a nostril into a nasal meatus adjacent a surface of a nasal concha.

FIG. 3B illustrates the extension of an energy delivery device from the apparatus into an interior of the nasal concha and the delivery of energy into the nasal concha.

FIG. 3C illustrates the immobilization of the apparatus within the nasal meatus and the cooling of the surface of the nasal concha during the delivery of energy to the nasal concha.

FIG. 4A illustrates the step of introducing ablative energy into an interior section of a nasal concha.

FIG. 4B illustrates an ablated tissue region and its absorption by the body.

FIG. 4C illustrates the resulting reduction in the size of the nasal concha.

DETAILED DESCRIPTION OF THE PREFERRED EMBODIMENT

The present invention provides a method and apparatus for ablating at least a portion of a nasal concha (turbinate). By ablating at least a portion of a nasal concha, the size of the nasal concha can be reduced. Accordingly, the present invention also provides a method for reducing the size of a nasal concha. The three nasal concha in the body (inferior, middle and superior nasal concha) form at least a portion of three nasal meatus (inferior, middle and superior nasal meatus). By reducing the size of a nasal concha, obstruction of a nasal meatus can be reduced. By reducing an obstruction of a nasal meatus, air flow through the nasal meatus is improved. Accordingly, the present invention also relates to a method for improving airflow through a nasal meatus of the body.

Figure 1:
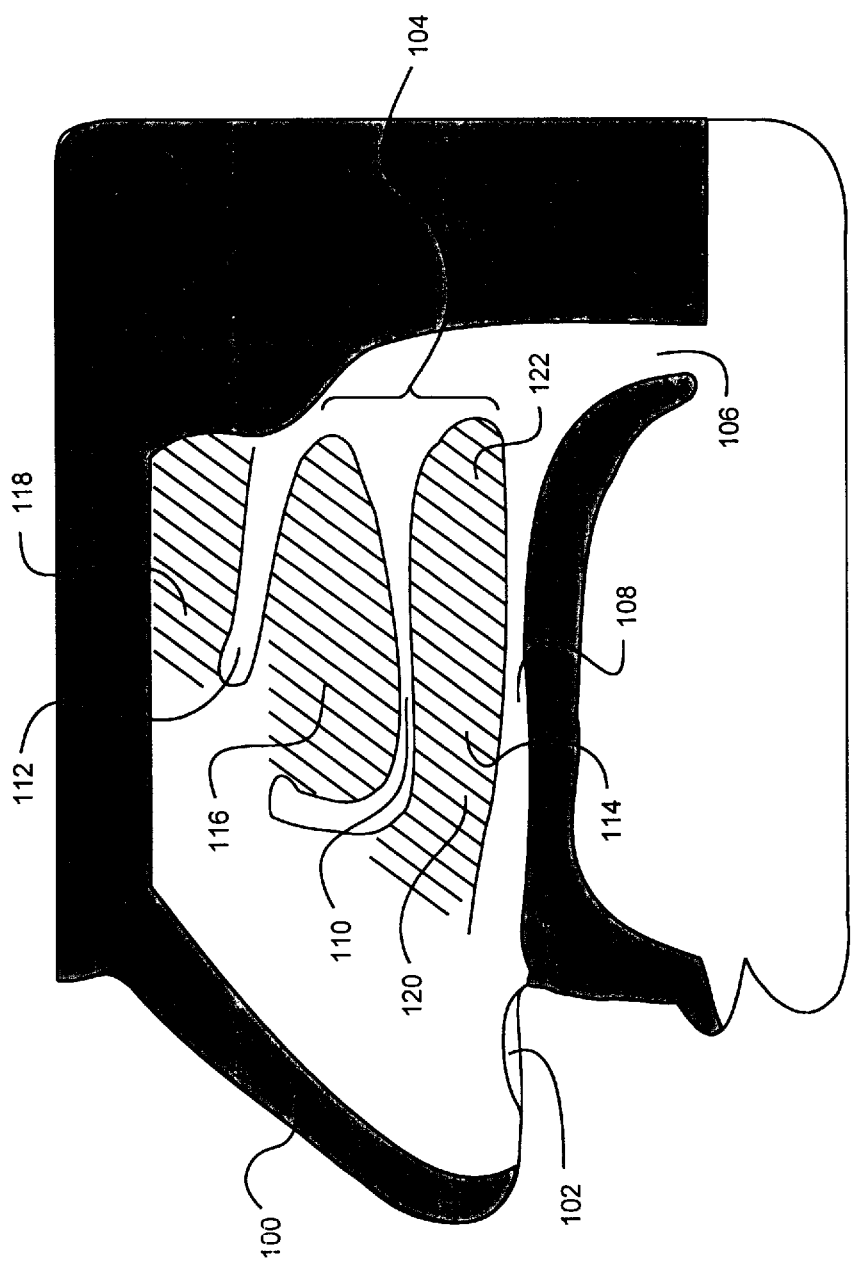
FIG. 1 illustrates the construction of the nasal passageways of the human nose.

FIG. 1 illustrates the construction of the nasal passageways of the human nose 100. As illustrated in the figure, the human nose includes a nostril 102 which leads into the nasal passageways from outside the body and a nasopharyngeal opening 104 which leads into the nasal passageways from the pharynx 106. Connecting the nostril 102 and nasopharyngeal opening 104 are a series of passageways, namely the inferior nasal meatus 108, the middle nasal meatus 110, and the superior nasal meatus 112. Forming at least a portion of each of these passageways are the nasal concha, also referred to as the turbinates. Forming at least a portion of the inferior nasal meatus 108 is the inferior nasal concha 114. Forming at least a portion of the middle nasal meatus 110 is the inferior nasal concha 114 and the middle nasal concha 116. Forming at least a portion of the superior nasal meatus 112 is the middle nasal concha 116 and the superior nasal concha 118. As also shown in FIG. 1, the inferior nasal concha 114 includes an anterior portion 120 which terminates adjacent the nasopharyngeal opening 104 and a posterior portion 122 which terminates adjacent the nostril 102.

Ablation of a nasal concha is accomplished according to the present invention by physically introducing an energy delivery device into an interior section of nasal concha tissue to deliver ablative energy therein. In the method and apparatus, the energy delivery device is designed to be minimally invasive such that the energy delivery device is introduced into the nasal concha without significantly injuring the surface of the nasal concha (aside from where the energy delivery device enters the nasal concha). For example, narrow bore needle-shaped probes for delivering energy may be used in the energy delivery device for insertion into the nasal concha.

The use of energy delivered by a minimally invasive means to ablate interior nasal concha tissue eliminates the need for surgical cutting to remove a portion of a nasal concha and the risks associated therewith. In particular, the procedure can be performed substantially bloodlessly and without having to expose tissue interior to the nasal concha, thereby significantly reducing the risk of infection.

Ablation can also be performed to remove an internal portion of the nasal concha without injuring the surface of the nasal concha (aside from where the energy delivery device enters the nasal concha). For example, by inserting the energy delivery device into the interior of the nasal concha and delivering energy to the nasal concha away from the surface of the nasal concha, interior tissue of the nasal concha can be ablated without simultaneously ablating the surface of the nasal concha. Cooling of the surface of the nasal concha may also be performed to prevent ablation of the surface of the nasal concha. As a result, the present invention provides a method and apparatus for reducing the size of a nasal concha without significantly injuring the surface of the nasal concha. By avoiding injury to the surface of the nasal concha, use of the apparatus of the present invention should be significantly less painful to the patient than traditional surgical methods for removing nasal concha tissue.

According to the present invention, it is preferred to ablate the inferior nasal concha 114, and more preferably an anterior portion 120 of the inferior nasal concha 114. In a preferred embodiment, the anterior portion 120 of the inferior nasal concha 114 is defined as being no larger than about one-third the volume of the inferior nasal concha 114. Thus, in one embodiment, the method includes ablating no more than about one-third of the inferior nasal concha 114.

FIG. 2 illustrates the effect enlargement of a nasal concha has on a nasal air passageway. As shown in FIG. 2, enlargement of the inferior nasal concha 114 can result in an obstruction of inferior nasal meatus 108. By reducing the size of the inferior nasal concha 114, illustrated in FIG. 2 by region below dashed line 123, the inferior nasal meatus 108 is reopened.

I. Method For Turbinate Ablation

Figure 3A:
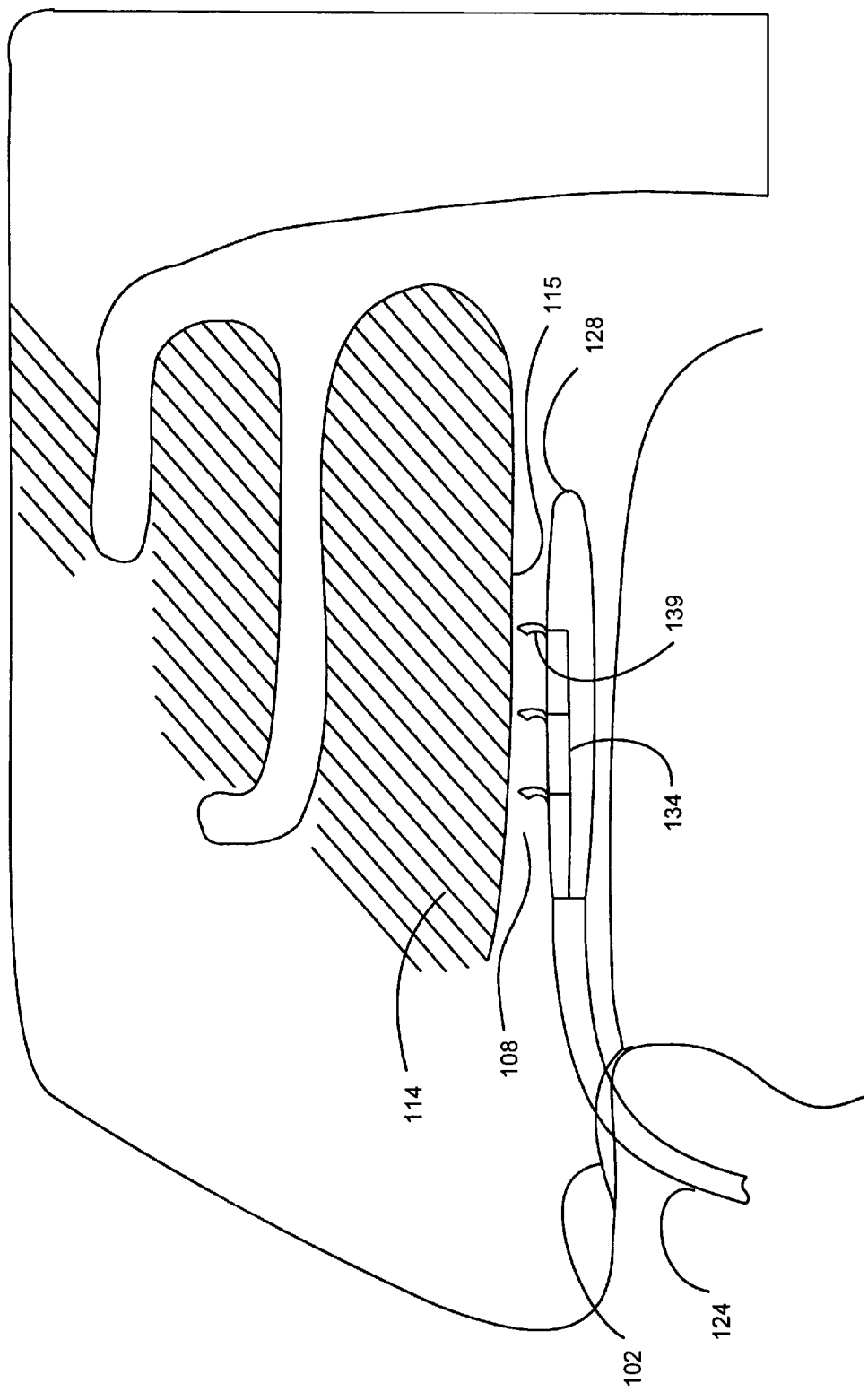
FIGS. 3A–3C illustrate an embodiment of a method for ablating a nasal concha.
Figure 3B:
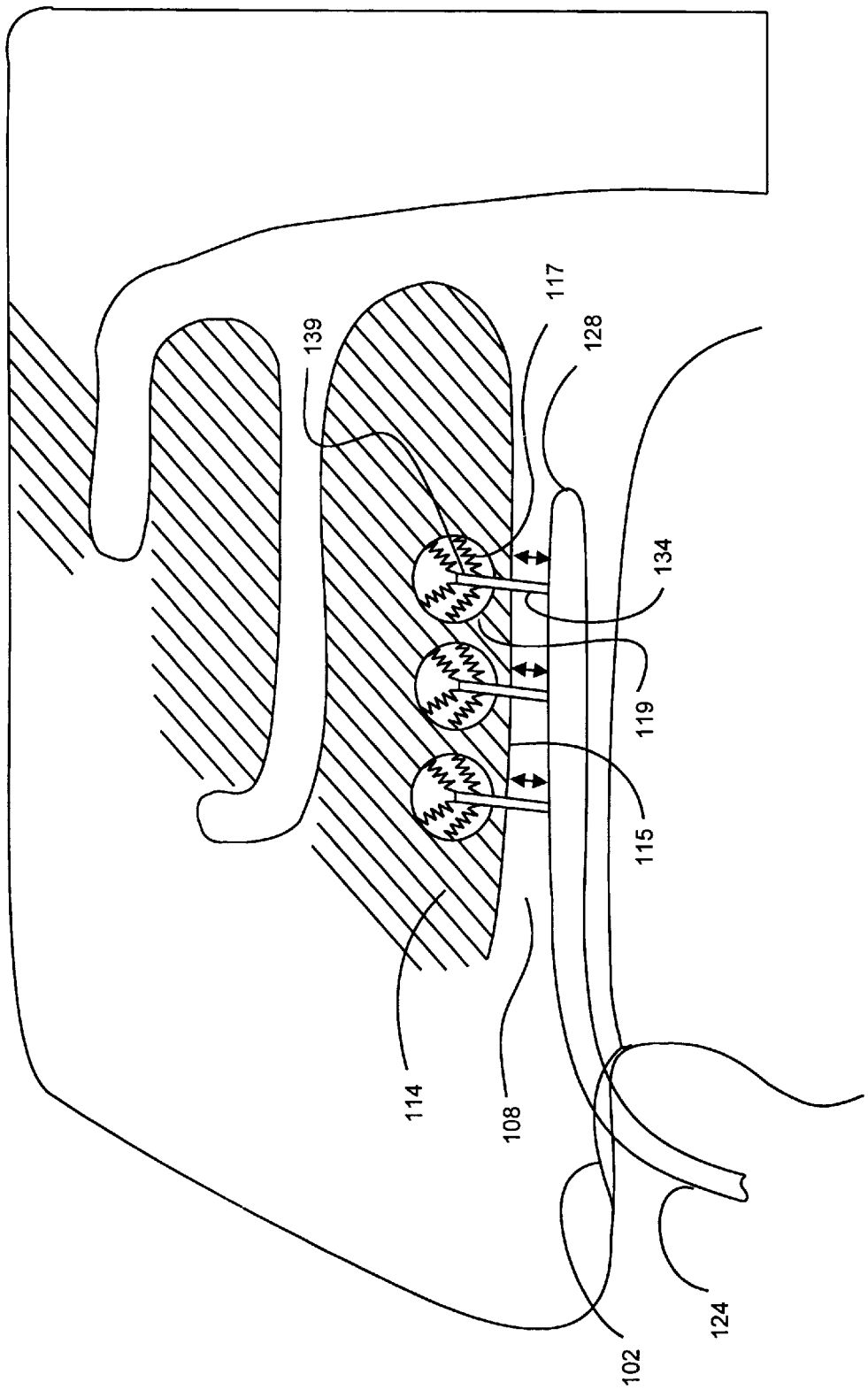
Figure 3C:
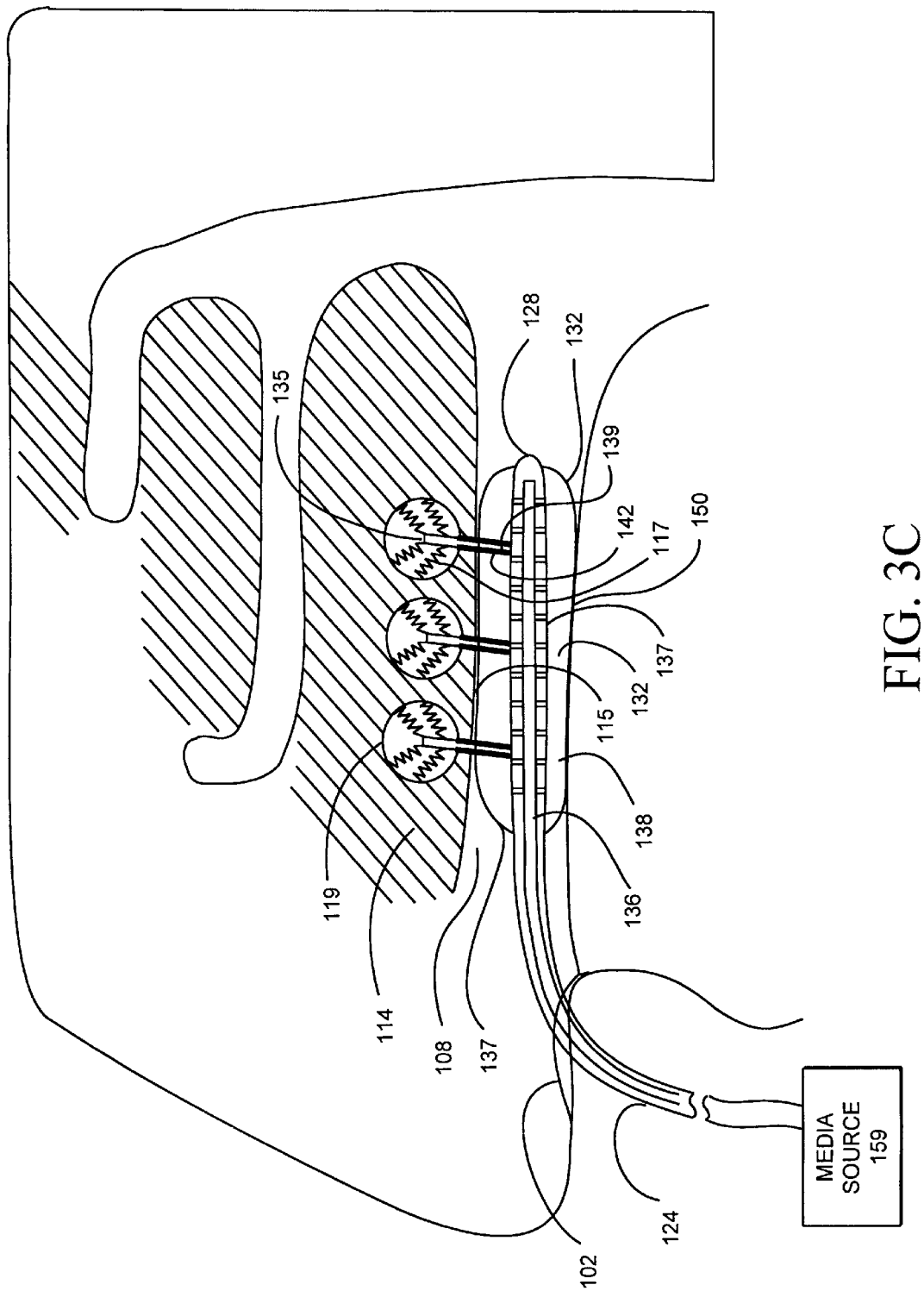

One aspect of the present invention relates to a method for ablating nasal concha tissue. FIGS. 3A–3C illustrate an embodiment of this method. As shown in FIG. 3A, an apparatus 124 having a distal portion 128 and an energy delivery device 134 for delivering ablative energy is introduced through a nostril 102 of a patient and into a nasal meatus adjacent a surface of a nasal concha, shown in FIGS. 3A–3C as the inferior nasal meatus 108 and the inferior nasal concha 114.

The energy delivery device 134 shown in the figures includes three probes 139 for delivering ablative energy. These probes are preferably contained within the distal portion 128 of the apparatus during introduction into the nasal meatus and are extended from the distal portion 128 after introduction.

As illustrated in FIG. 3B, the probes 139 are delivered through the surface 115 of the nasal concha 114 and into an interior section of the nasal concha. The apparatus may be designed such that the probes of the energy delivery device 134 extend a fixed length from the apparatus. Alternatively, as illustrated in FIG. 3B by arrow (⇆), the energy delivery device 134 may be designed to be at least partially extendable from the distal portion 128 and/or at least partially retractable into the distal portion 128.

Once the probes 139 of the energy delivery device 134 are positioned within the nasal concha, ablative energy 117 is delivered through the apparatus and the energy delivery device 134 to an area 119 of the nasal concha 114 adjacent the probes 139. Sufficient energy 117 is delivered during this step to ablate at least a portion of the nasal concha 114.

According to this method, the ablative energy may be any form of energy capable of causing the ablation of tissue by heating at least a portion of the nasal concha being treated to a temperature above about 40° C. Examples of types of energy that may be used include, but are not limited to energy from a diode laser ablation, a laser fiber (defused), microwave (915 MHz and 2.45 GHz), ultrasound, and RF at all relevant frequencies. In a preferred embodiment, the energy is electromagnetic energy and is preferably RF radiation or microwave radiation. Illustrated in FIG. 3B are a series of RF electrodes 139 as the energy delivery device 134. The invention is also intended to encompass the use of probes designed to deliver different forms of energy.

When the energy used is RF radiation, the energy preferably has a frequency between about 300 megahertz and about 700 megahertz. The RF energy delivered to the nasal concha is preferably sufficient to deliver between about 5 and about 30 watts of RF energy to at least a portion of the nasal concha being treated.

The apparatus of the present invention may be designed to be immobilized within the nasal meatus. This may be accomplished, for example, by including an expandable member on the apparatus distal portion 128, illustrated in FIG. 3C and FIG. 6 as element 132.

When expanded within the nasal meatus 108, the expandable member 132 serves to immobilize the apparatus distal portion 128 relative to the nasal concha 114 to be ablated. Accordingly, the method may optionally further include the step of immobilizing the apparatus distal portion relative to the nasal concha. Further, when the apparatus includes an expandable member, the step of immobilizing the apparatus within the nasal meatus may include the step of expanding the expandable member within the nasal meatus.

The surface 115 of the nasal concha 114 may also be cooled during the delivery of energy 117. Cooling the surface 115 of the nasal concha 114 may be accomplished, for example, by cooling the distal portion 128 of the apparatus within the nasal meatus. As illustrated in FIG. 3C, the apparatus may include an expandable member 132 attached to the apparatus at the distal portion 128. In this embodiment, the apparatus also includes a lumen 136 coupled to the apparatus for delivering a medium 138 through apertures 137 in the lumen 136 to expand the expandable member 132. The medium is delivered from a media source 159 through the lumen 136 to within the expandable member 132. During ablation, cool media may be delivered from the media source 159 into the expandable member to cool the surface 115 of the nasal concha.

Cooling the surface of the nasal concha being treated with energy serves at least two purposes. Cooling may be used to prevent ablation of the surface 115 of the nasal concha 114 by preventing the surface 115 from reaching a temperature at which the tissue becomes ablated. In this regard, it is preferred that the cooling be sufficient to prevent the surface tissue of the nasal concha from exceeding a temperature of about 40° C.

Cooling may also be used to control the location of the ablation site. For example, cooling the nasal concha surface enables the formation of an entirely internal ablation site. The extent of cooling provided, in combination with the positioning of the energy delivery device 134 and the amount of energy delivered, can be used to control the thickness of non-ablated tissue between the surface of the nasal concha and the internal ablation site.

According to the method, the nasal meatus into which the apparatus is delivered may be the inferior, middle and/or superior nasal meatus and is preferably the inferior nasal meatus. The nasal concha ablated may be the inferior, middle and/or superior nasal concha and is preferably the inferior nasal concha. In one embodiment, energy is delivered to a selected section of one of the nasal concha. For example, energy may be selectively delivered to the anterior or posterior sections of the inferior nasal concha. Delivery of energy to a selected section of a nasal concha may be accomplished by the placement of the apparatus within the nasal meatus. The delivery of energy to a selected section of a nasal concha may also be accomplished by insulating at least a portion of the nasal concha from ablative energy.

As also illustrated in FIG. 3C, an insulative covering 142 may be positioned over a portion of the energy delivery device 134 to control the delivery of energy to a selected section of tissue. The positioning of the insulative covering 142 may be adjustable relative to the energy delivery device 134. Accordingly, the method may optionally include the further step of delivering energy to a portion of a nasal concha while insulating another portion of the nasal concha. The method may also optionally include the step of adjusting the position of the insulating covering 142 relative to the energy delivery device 134.

The present invention also relates to a method for reducing the size of a nasal concha. According to the method, the size of a nasal concha is reduced by ablating tissue forming a nasal concha and removing the ablated nasal concha tissue. Removal of the ablated nasal concha tissue is preferably accomplished by natural absorption of ablated tissue by the patient's body.

Figure 4A:
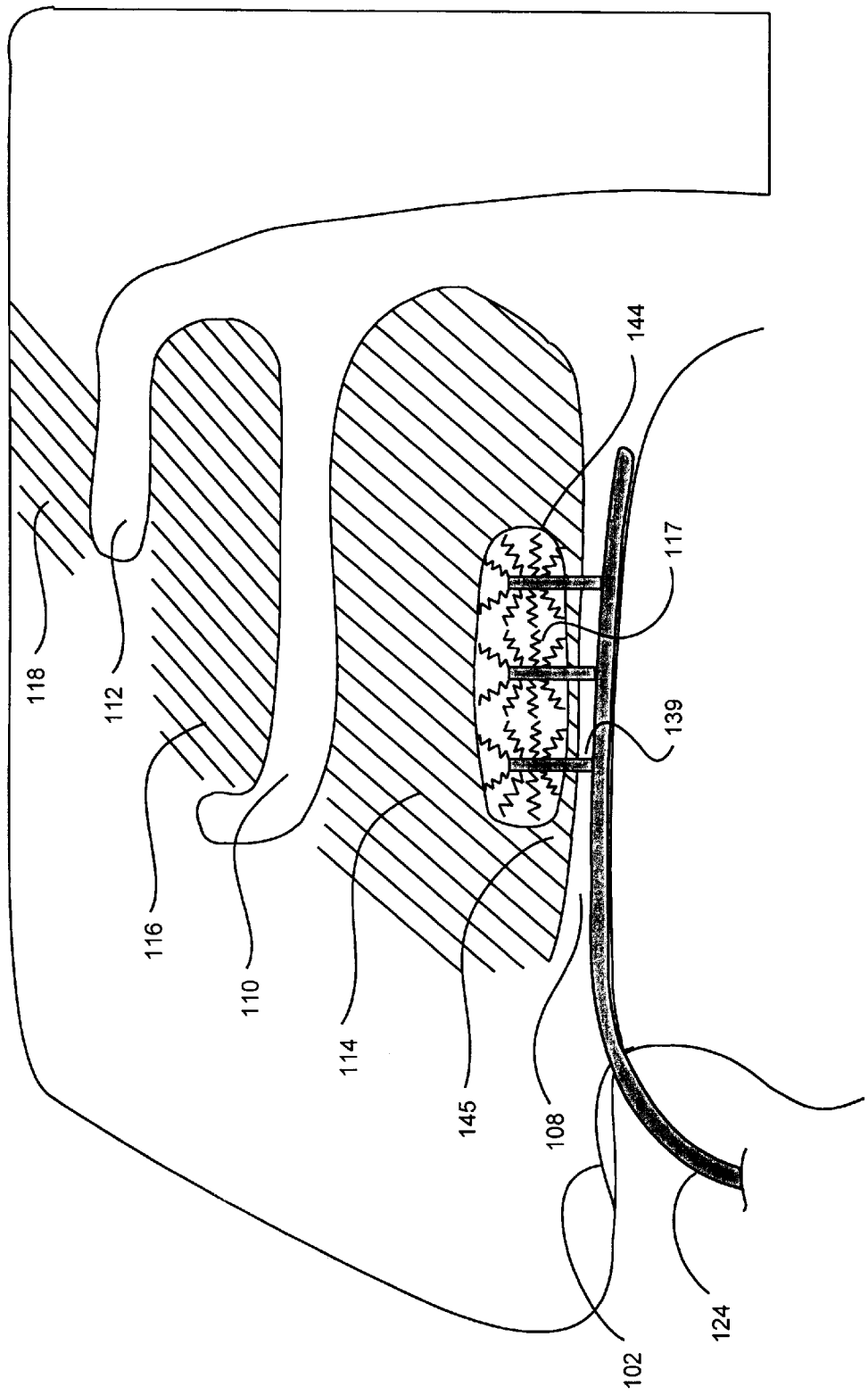
FIGS. 4A–C illustrate the steps of ablating a portion of a nasal concha according to the present invention.
Figure 4B:
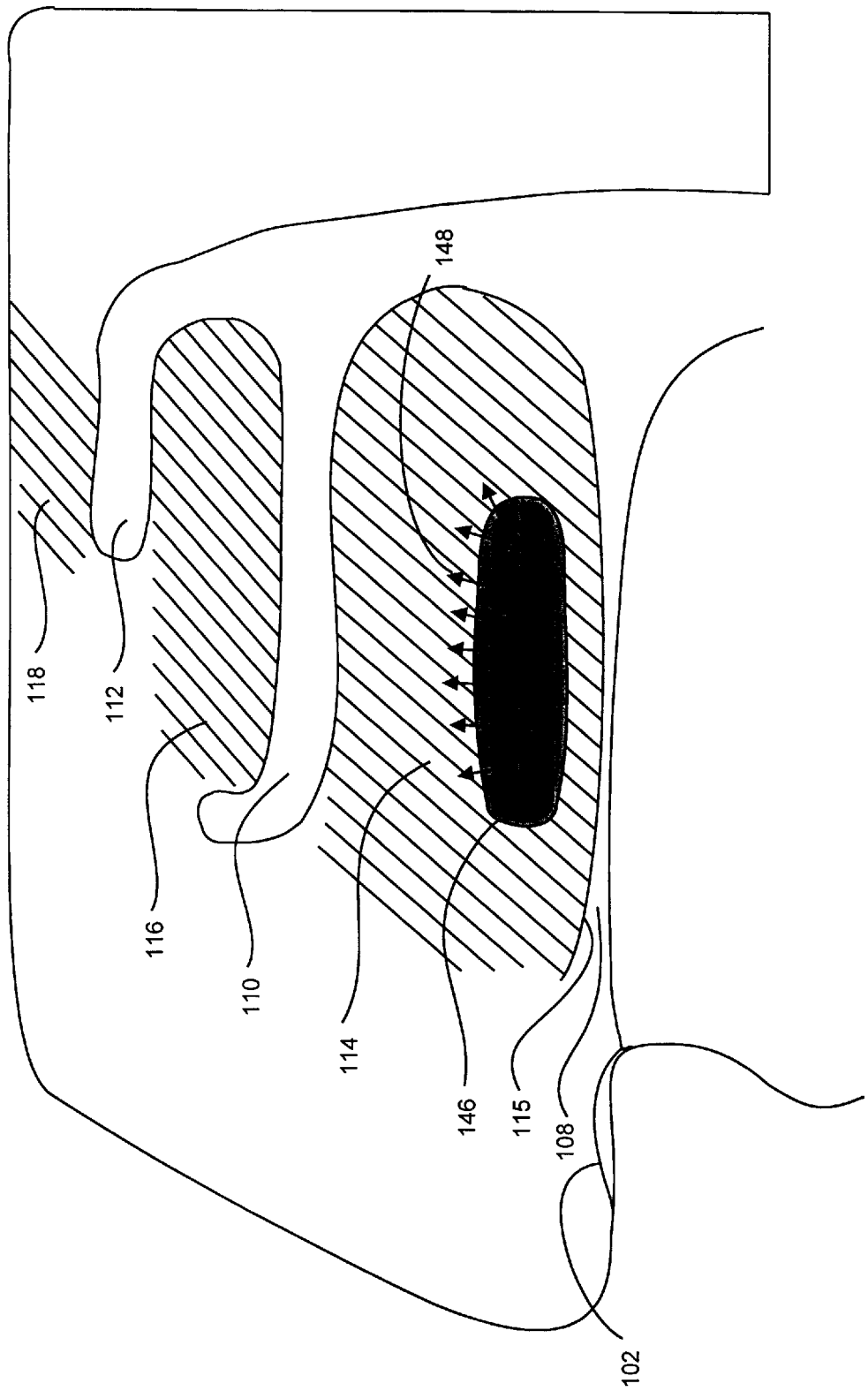
Figure 4C:
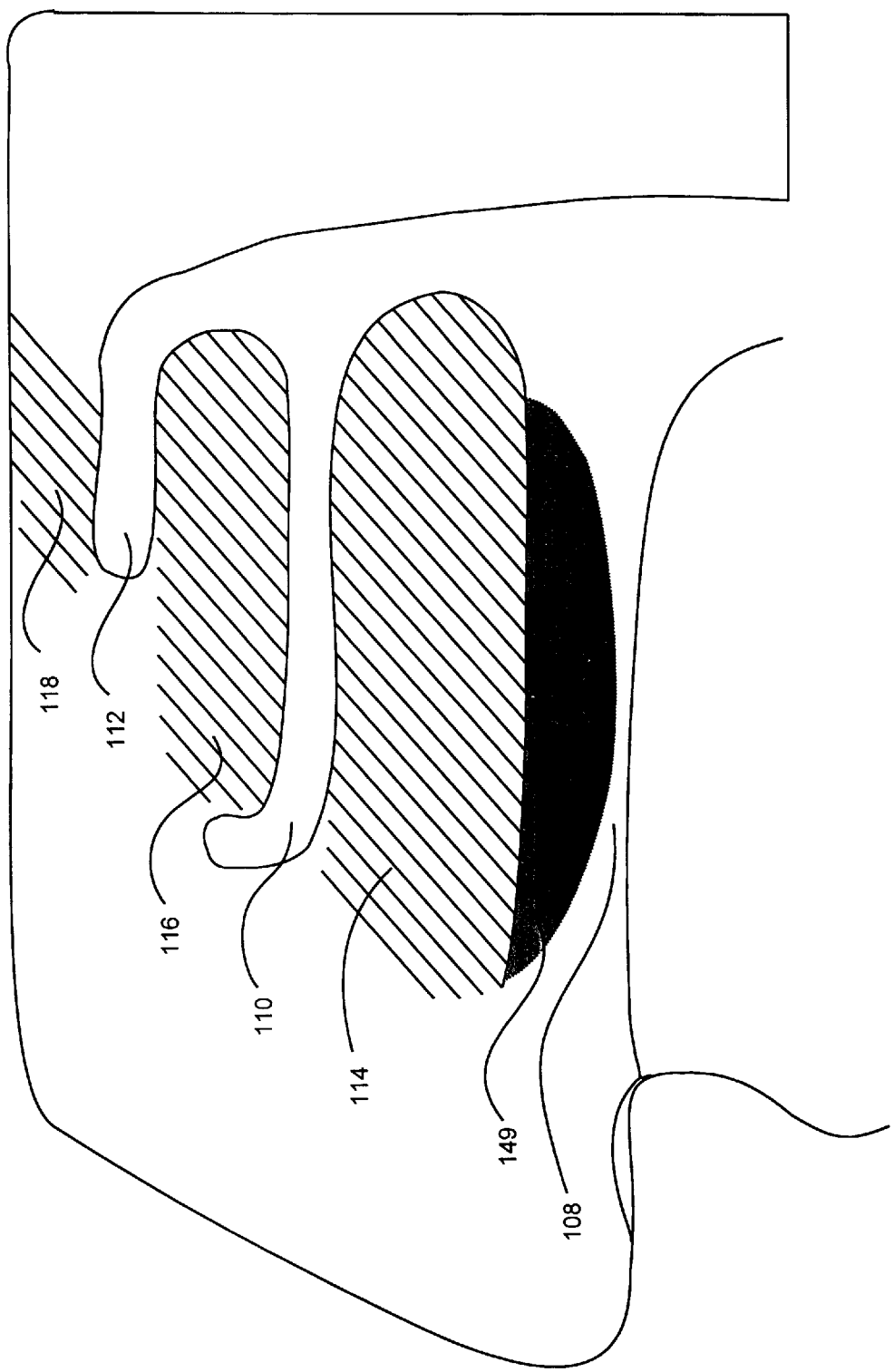

FIGS. 4A–C illustrate the removal of an internal region of tissue by ablation. FIG. 4A illustrates introducing ablative energy 117 via energy delivery device probes 139 into an interior section 144 of a nasal concha 114. Cooling of the surface 115 of the nasal concha 114 may be performed in order to prevent the ablation of the surface of the nasal concha.

FIG. 4B illustrates the absorption (illustrated by arrows 148) of a region 146 of ablated tissue by the body. As illustrated in FIG. 4B, the ablated tissue region 146 is an interior region, i.e., the surface 115 of the nasal concha is not ablated. This may be achieved by cooling the surface 115 of the nasal concha during the delivery of ablative energy to the nasal concha. It may also be achieved by controlling the positioning of the energy delivery device 134 relative to the surface 115 and by controlling the amount of energy delivered by the energy delivery device 134.

FIG. 4C illustrates the resulting reduction in the size of the nasal concha after absorption. Region 149 illustrates the volume of tissue that is removed from the path of the nasal meatus by this method. As can be seen by comparing FIGS. 4A and 4C, the size of nasal meatus 108 is enlarged by this process.

The present invention also relates to a method for improving airflow through a nasal meatus by reducing the size of a nasal concha which defines at least a portion of the nasal meatus. This method can be accomplished by the method for reducing the size of a nasal concha as described above. In one embodiment, the rate of airflow through the nasal meatus at a given pressure is increased by at least 25%.

2. Turbinate Ablation Apparatus

Figure 5:
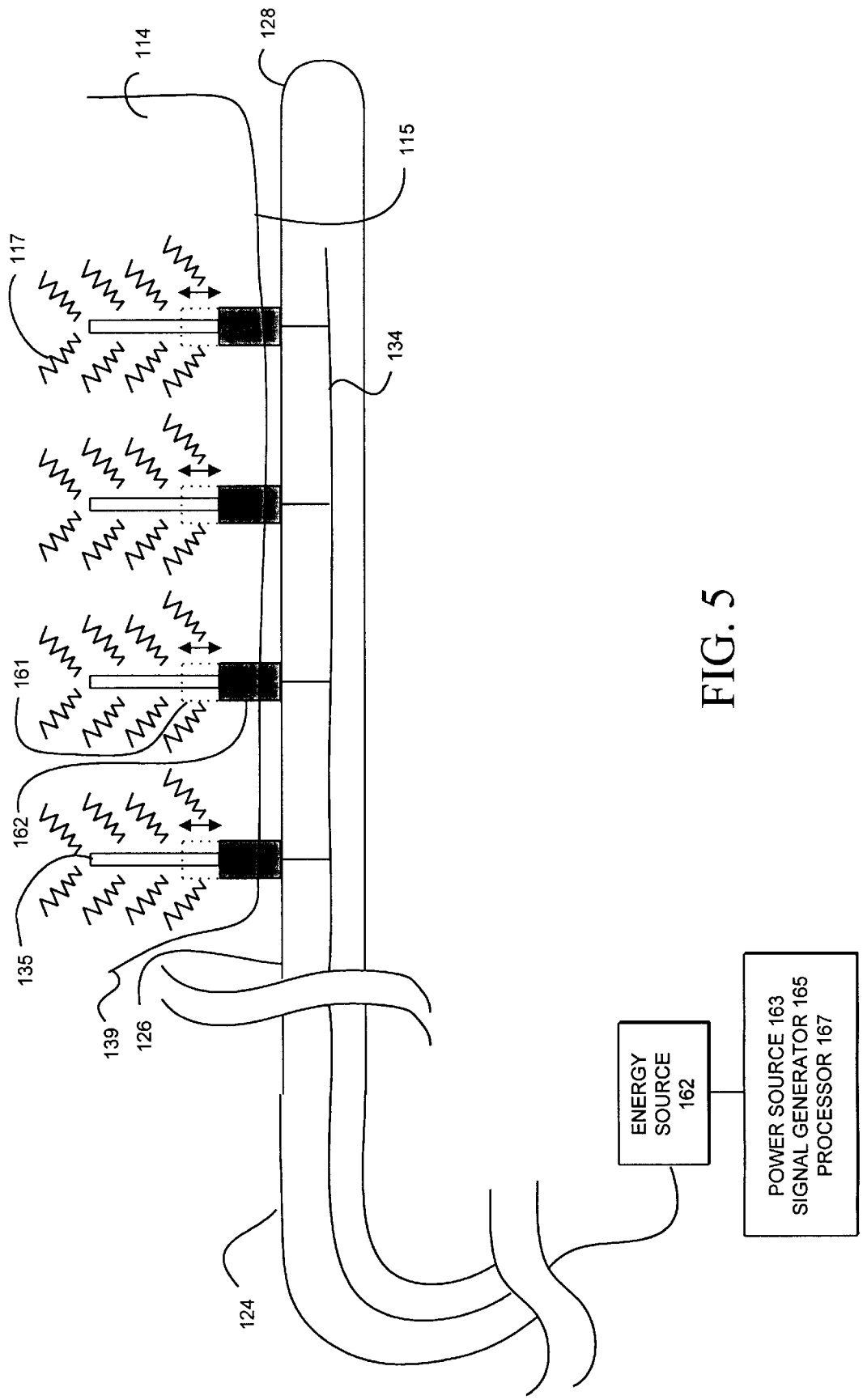
FIG. 5 illustrates an apparatus according to the present invention.

The present invention also relates to an apparatus for ablating a nasal concha. As illustrated in FIG. 5, the apparatus 124 includes a catheter 126 which has a distal portion 128 with dimensions configured for introduction through a nostril of a patient into a nasal meatus of a patient.

The apparatus also includes an energy delivery device 134. The energy delivery device 134 is illustrated in the figure as including a plurality of probes 139 designed to pierce the nasal concha and deliver ablative energy therein. In order to facilitate the entry of the probes into the nasal concha, each probe preferably includes a pointed distal end 135.

The probes 139 of the energy delivery device 134 may extend a fixed distance from the catheter distal portion 128. In such case, the probes 139 should extend from the catheter distal portion 128 a sufficient distance necessary to ablate an interior portion of the nasal concha 114. Alternatively, as illustrated in FIG. 5 by the arrow (⇆), the energy delivery device 134 may be designed to be at least partially extendable from the catheter distal portion 128 and/or at least partially retractable into the catheter distal portion 128.

The energy delivery device 134 should also be configured to selectively introduce the probes into the nasal concha or a selected subregion of the nasal concha. Accordingly, when a plurality of probes 139 are used as illustrated in FIG. 5, the probes should be positioned relative to the catheter distal portion 128 so that the probes 139 are all introduced into the nasal concha and not into other tissue adjacent the nasal concha.

The probes 139 used in the energy delivery device 134 may be any probe which can pierce the surface of a nasal concha and which can deliver a form of energy capable of causing the ablation of tissue. Ablation is preferably performed by heating at least a portion of the nasal concha to be treated to a temperature above about 40° C. Examples of types of energy that may be used include, but are not limited to energy from a diode laser ablation, a laser fiber (defused), microwave (915 MHz and 2.45 GHz), ultrasound, and RF at all relevant frequencies. In a preferred embodiment, the energy is electromagnetic energy and is preferably RF radiation or microwave radiation delivered into the nasal concha by one or more needle electrodes.

When the energy is RF radiation, the energy preferably has a frequency between about 300 megahertz and about 700 megahertz. The RF energy delivered to the nasal concha is preferably sufficient to deliver between about 5 and about 30 watts of RF energy to at least a portion of the nasal concha being treated.

As illustrated in FIG. 5, the energy delivery device may optionally include an insulator 162 surrounding each probe 139 which prevents the delivery of ablative energy 117 through at least a portion of the probe 139. As illustrated in FIG. 5, by the dashed lines 161, the insulator 162 may be moved relative to the energy delivery device 134 to cause energy to be delivered to a selected section of a nasal concha while preventing the ablation of another selected section of tissue.

Figure 6:
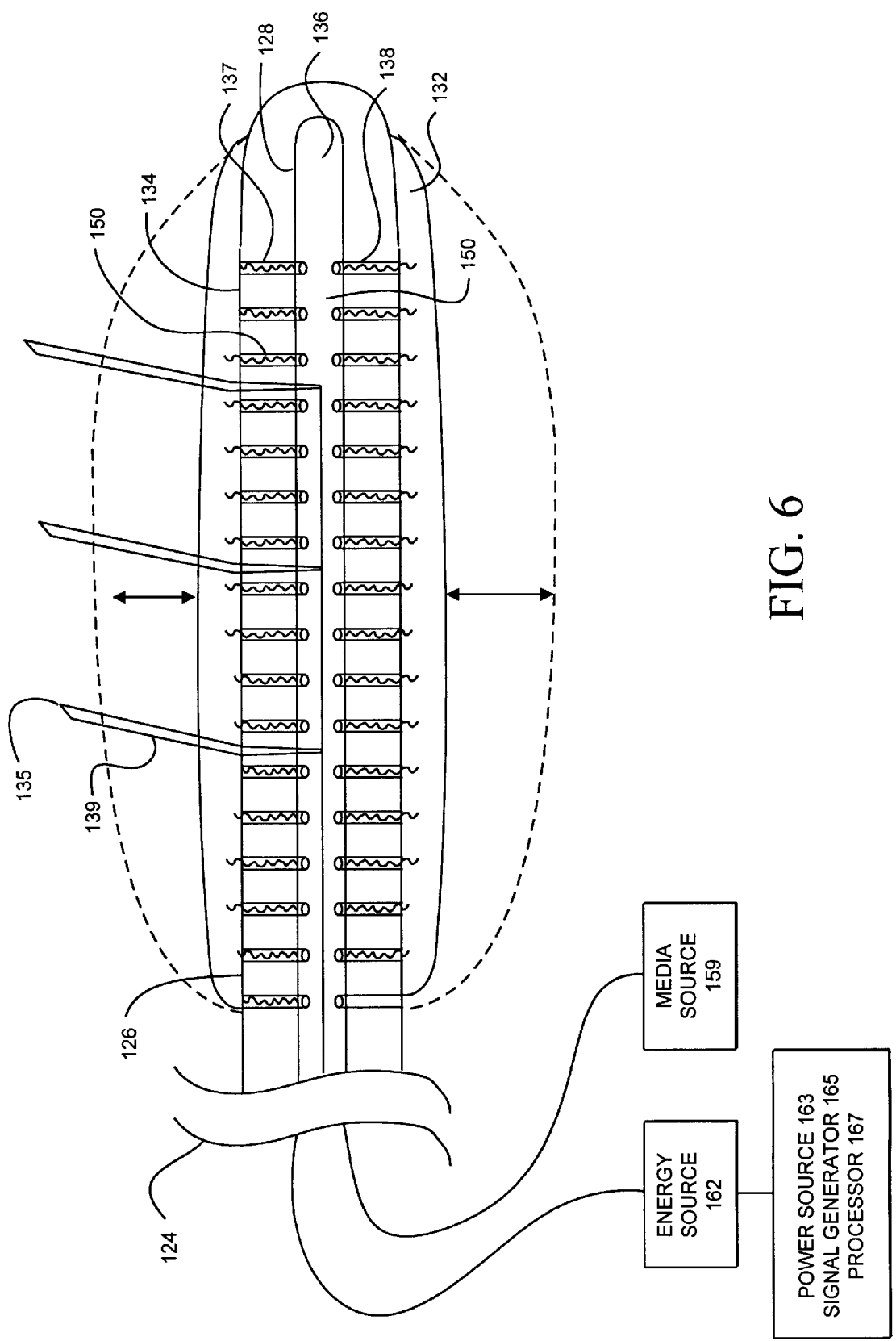
FIG. 6 illustrates an apparatus according to the present invention with an expandable member for immobilizing the apparatus within a nasal meatus.

As illustrated in FIG. 6, an expandable member 132 may be attached to the catheter 126 at the catheter distal portion 128. The expandable member can be used to immobilize the catheter distal portion 128 within the nasal meatus by expanding against the walls forming the nasal meatus. The expandable member preferably conforms to a contour of the nasal meatus when expanded. In one embodiment, the expandable member conforms to the surface of the nasal concha when expanded.

A variety of mechanisms are known in the art which may be used to expand the expandable member 132. One mechanism, illustrated in FIG. 6, involves the use of a lumen 136 coupled with the catheter 126 for delivering a medium 138 to expand the expandable member 132. The medium is delivered from a media source 159 through the lumen 136 to within the expandable member 132 through apertures 137. The apertures 137 may be formed by a sheath 150 which substantially surrounds the lumen 136. In one embodiment, the sheath 150 is formed of a relatively inert and relatively hard substance, such as metallic copper or metallic silver. In alternative embodiments, the sheath 150 includes some other inert substance, such as gold, stainless steel, titanium, various plastic compounds, or some combination thereof.

The expandable member illustrated in FIG. 6 can also be used to cool the surface of a nasal concha being ablated. Cooling may be accomplished by introducing cool medium into the expandable member. This may be accomplished, for example, by including a cooling mechanism into the media source 159 to cool the media.

As illustrated in FIG. 5, ablative energy is supplied to the energy delivery device by an energy source 162. As discussed above, a variety of forms of ablative energy may be used in the present invention. Accordingly, the energy source is selected to provide the desired form of energy.

In one embodiment, the energy source 162 includes an energy source 163 (or a power regulator coupled to a standard energy source such as a wall socket or battery), a signal generator 165 (such as a generator for pulses, sine waves, square waves, or some combination of these wave forms with each other or with some other wave form), and a processor 167 for controlling the signal generator.

In a preferred embodiment, the signal generator generates pulses of RF energy having an RF radiation frequency between about 300 megahertz and about 700 megahertz, such as preferably about 465 megahertz. In alternative embodiments, the RF energy may have an RF radiation frequency in the microwave range or in another range of the electromagnetic spectrum.

The processor controls the amount of energy delivered by the apparatus. In this embodiment, the apparatus can further include a signal generator coupled to the energy delivery device and coupled to a energy source. The apparatus can also include a processor coupled to the signal generator and disposed for controlling the signal generator. According to this embodiment, the processor can control the way in which energy is delivered. For example, the signal generator can generate pulses of RF energy which provide between about 5 watts and about 30 watts of RF energy to at least a portion of the turbinate. The processor can also control the amount of energy produced so that the region of turbinate tissue to be ablated is heated to a temperature of at least 40° C.

In order to monitor the amount of energy delivered and the amount of heat generated, the apparatus can also include one or more sensors. These sensors can be used to detect a variety of operating parameters including the amount of energy delivered, the impedance generated, and the temperature of a region adjacent the apparatus. These sensors can also be used to provide feedback for controlling the operation of an energy source which delivers energy to the energy delivery device. In addition, chemical or biochemical sensors can be used to detect ablation.

In one embodiment, the apparatus includes at least one temperature sensor, such as a thermocouple or thermistor. The temperature sensor is coupled to a communication link (such as a conductor), which is coupled to the processor. For example, in the case where the temperature sensor is a thermocouple, the communication link may comprise a D/A converter coupled to a register disposed for reading by the processor. The processor reads an sensor value from the sensor and, responsive thereto, controls the signal generator so as to achieve delivery of an effective amount of RF energy to a desired section of tissue to be ablated. The processor thus uses the signal generator, catheter distal portion, energy delivery device, and temperature sensor, as a feedback loop for controlled delivery of RF energy to a section of a nasal concha. For example, the processor may control the delivery of RF energy to achieve delivery of a selected amount of energy, to achieve a selected temperature, or to achieve a selected amount of ablation of a section of a nasal concha. A variety of positionings for the sensors are possible. In one embodiment, the sensor is coupled to the expandable member.

Figure 7:
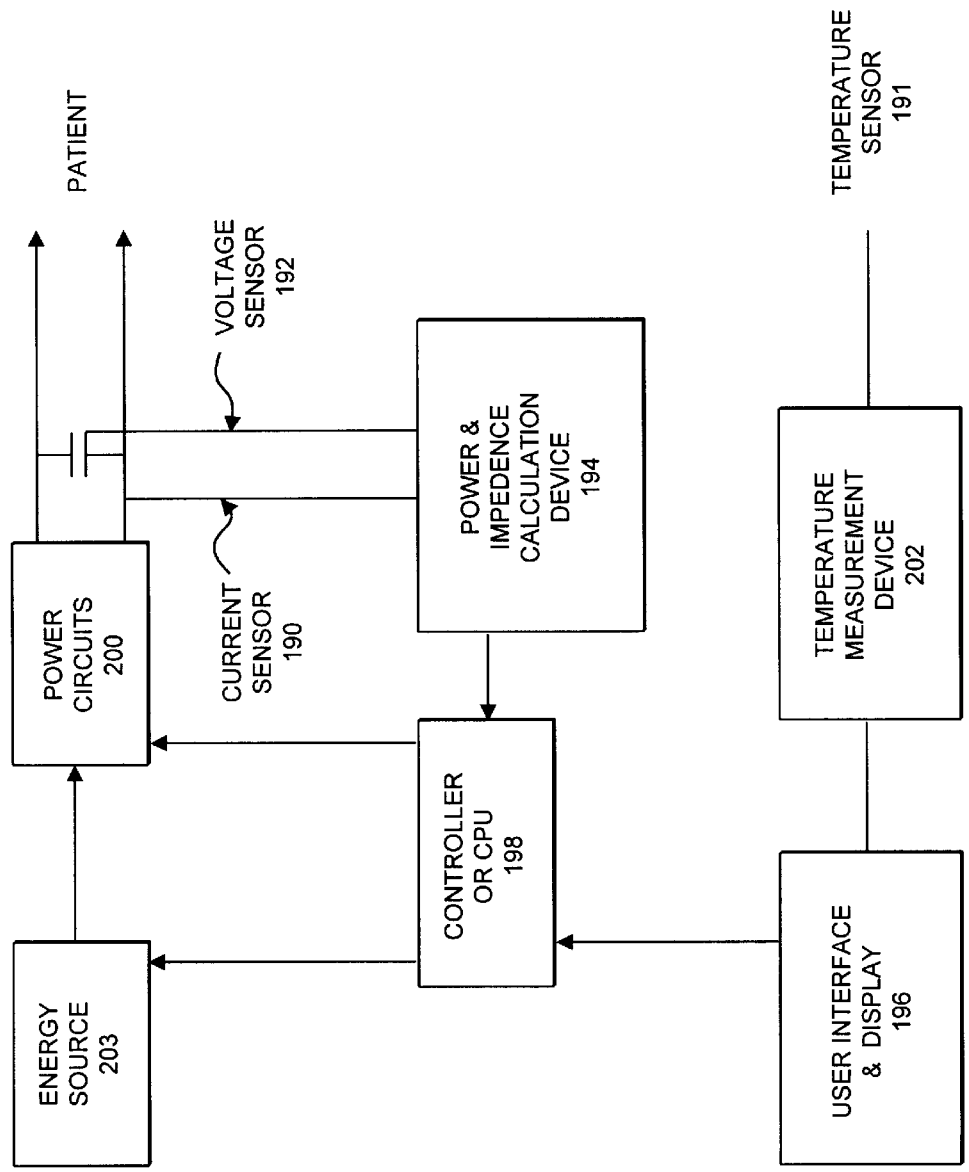
FIG. 7 is a block diagram of a feedback control system useful with the method and apparatus of the present invention.
Figure 8:
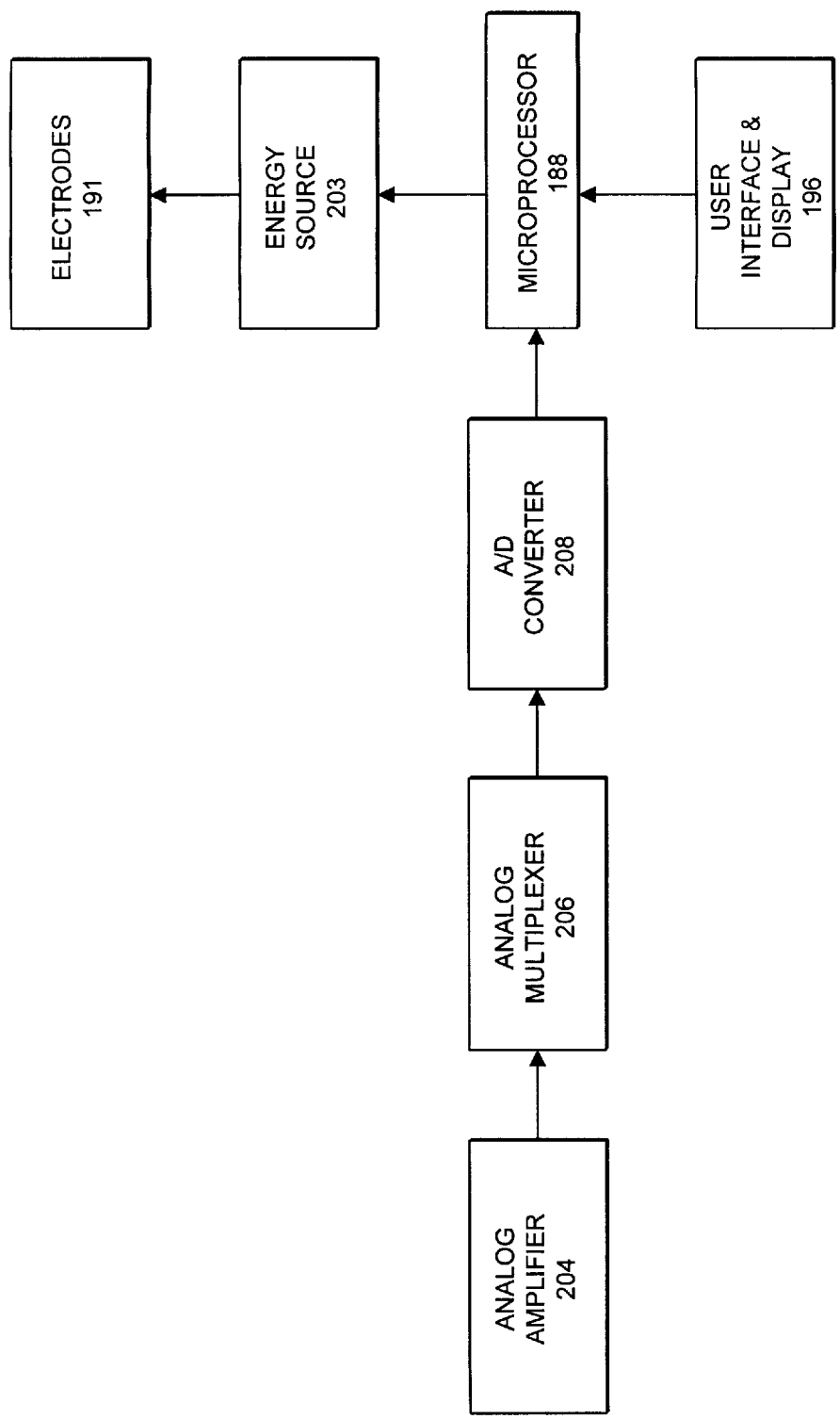
FIG. 8 is a block diagram illustrating an analog amplifier, analog multiplexer and microprocessor used with the feedback control system of FIG. 7.

As described above, the temperature or some other property of the tissue being ablated, or of the energy delivery device can be monitored using a variety of sensors. Illustrated in FIGS. 7 and 8 is an open and a closed loop feedback system for coupling a sensor used in the apparatus to an energy source so that the output energy of the energy source is adjusted in relation to the property sensed by the sensor. The feedback system, is described herein with regard to the delivery of RF energy. It should be noted, however, that the feedback system can be readily adjusted for use with a variety of other types of energy, such as microwaves.

Using the feedback system, the physician can, if desired, override the closed or open loop system. A microprocessor can be included and incorporated in the closed or open loop system to switch energy on and off, as well as modulate the energy. The closed loop system utilizes a microprocessor to serve as a controller, watch the temperature, adjust the amount of energy being delivered, look at the result, re-feed the result, and then modulate the energy.

In the case of RF energy, the sensors and feedback control system can be used to, maintained tissue adjacent to an energy delivery device at a desired temperature for a selected period of time without impeding out. An output maintains the energy delivered to the energy delivery device for a selected length of time.

As illustrated in FIG. 7, current is delivered through energy delivery device 189 is measured by current sensor 190. Voltage is measured by voltage sensor 192. Impedance and energy are then calculated at energy and impedance calculation device 194. These values can then be displayed at a user interface and display 196. Signals representative of energy and impedance values are received by a controller 198.

A control signal is generated by controller 198 that is proportional to the difference between an actual measured value, and a desired value. The control signal is used by energy circuits 200 to adjust the energy output in an appropriate amount in order to maintain the desired energy delivered at each energy delivery device 189.

In a similar manner, temperatures detected at temperature sensors 191 provide feedback for maintaining a selected energy. The actual temperatures are measured at temperature measurement device 202, and the temperatures are displayed at user interface and display 196. A control signal is generated by controller 198 that is proportional to the difference between an actual measured temperature, and a desired temperature. The control signal is used by energy circuits 200 to adjust the energy output in an appropriate amount in order to maintain the desired temperature delivered at the respective sensor. A multiplexer can be included to measure current, voltage and temperature, at numerous sensors, and energy can be delivered to the energy delivery device 189 in monopolar or bipolar fashion.

Controller 198 can be a digital or analog controller, or a computer with software. When controller 198 is a computer it can include a CPU coupled through a system bus. On this system can be a keyboard, a disk drive, or other non-volatile memory systems, a display, and other peripherals, as are known in the art. Also coupled to the bus is a program memory and a data memory.

User interface and display 196 includes operator controls and a display. Controller 198 can be coupled to imaging systems, including but not limited to ultrasound, CT scanners, X-ray, MRI, mammographic X-ray and the like. Further, direct visualization and tactile imaging can be utilized.

The output of current sensor 190 and voltage sensor 192 is used by controller 198 to maintain a selected energy level at energy delivery device 189. The amount of energy delivered controls the amount of energy. A profile of energy delivered can be incorporated in controller 198, and a preset amount of energy to be delivered can also be profiled.

Circuitry, software and feedback to controller 198 result in process control, and the maintenance of the selected energy that is independent of changes in voltage or current, and are used to change, (i) the selected energy, (ii) the duty cycle (on-off and wattage), (iii) bipolar or monopolar energy delivery, and (iv) infusion medium delivery, including flow rate and pressure. These process variables are controlled and varied, while maintaining the desired delivery of energy independent of changes in voltage or current, based on temperatures monitored at sensors 191.

Current sensor 190 and voltage sensor 192 are connected to the input of an analog amplifier 204. Analog amplifier 204 can be a conventional differential amplifier circuit for use with temperature sensors 191. The output of analog amplifier 204 is sequentially connected by an analog multiplexer 206 to the input of AND converter 208. The output of analog amplifier 204 is a voltage which represents the respective sensed temperatures. Digitized amplifier output voltages are supplied by A/D converter 208 to microprocessor 188. Microprocessor 188 may be a type 68HCII available from Motorola. However, it will be appreciated that any suitable microprocessor or general purpose digital or analog computer can be used to calculate impedance or temperature.

Microprocessor 188 sequentially receives and stores digital representations of impedance and temperature. Each digital value received by microprocessor 188 corresponds to different temperatures and impedances.

Calculated energy and impedance values can be indicated on user interface and display 196. Alternatively, or in addition to the numerical indication of energy or impedance, calculated impedance and energy values can be compared by microprocessor 188 with energy and impedance limits. When the values exceed predetermined energy or impedance values, a warning can be given on user interface and display 196, and additionally, the delivery of RF energy can be reduced, modified or interrupted. A control signal from microprocessor 188 can modify the energy level supplied by energy source 203

Figure 9:
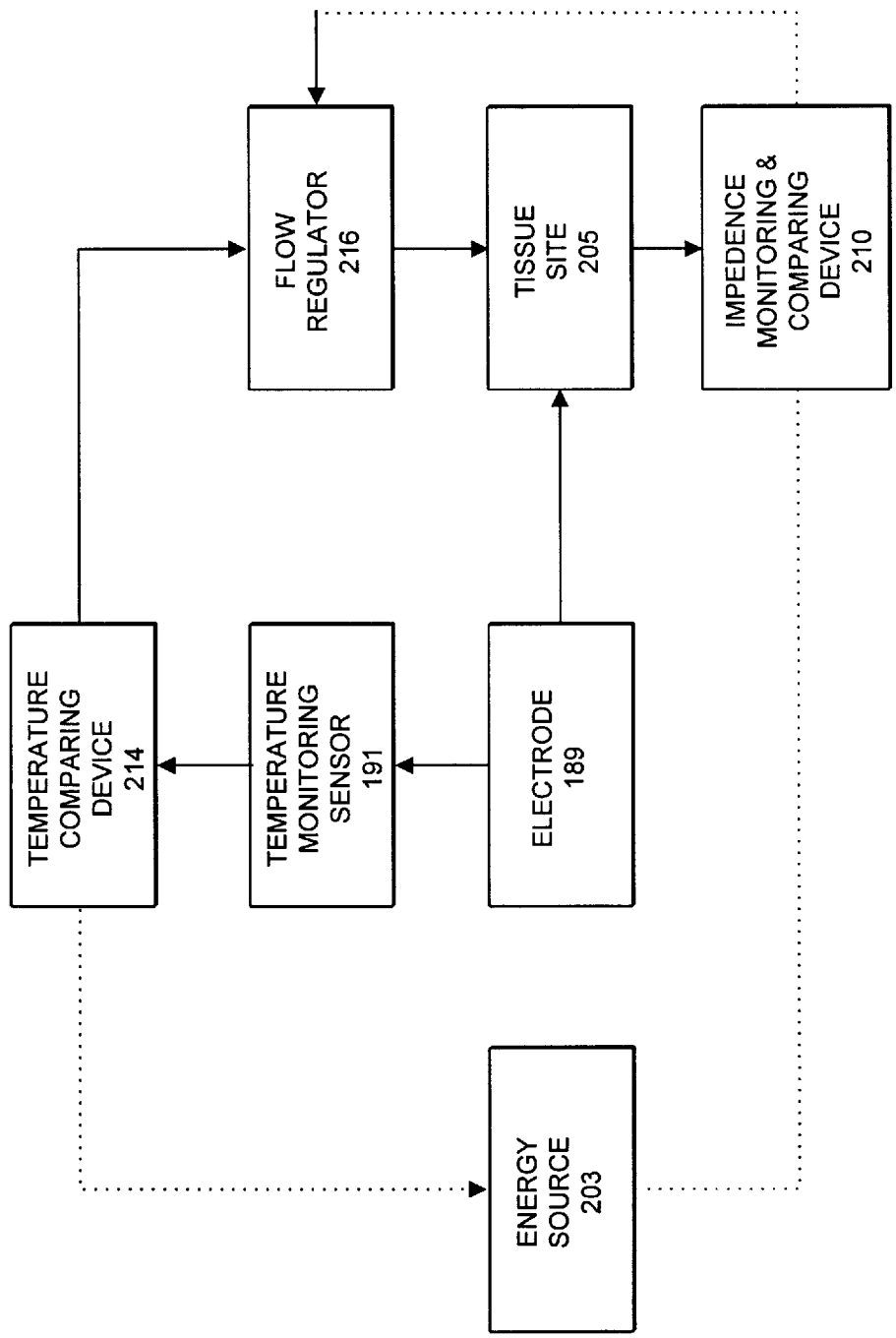
FIG. 9 is a block diagram of a temperature/impedance feedback system that can be used to control cooling medium flow rate through an apparatus of the present invention.

FIG. 9 illustrates a block diagram of a temperature/impedance feedback system that can be used to control cooling medium flow rate through the catheter into the expandable member. Ablative energy is delivered to energy delivery device 189 by energy source 203, and applied to tissue. A monitor 210 ascertains tissue impedance, based on the energy delivered to tissue, and compares the measured impedance value to a set value. If the measured impedance exceeds the set value a disabling signal 211 is transmitted to energy source 203, ceasing further delivery of energy to the energy delivery device 189. If measured impedance is within acceptable limits, energy continues to be applied to the tissue. During the application of energy to tissue sensor 191 measures the temperature of tissue and/or energy delivery device 189. A comparator 214 receives a signal representative of the measured temperature and compares this value to a pre-set signal representative of the desired temperature. Comparator 214 sends a signal to a flow regulator 216 representing a need for a higher cooling medium flow rate, if the tissue temperature is too high, or to maintain the flow rate if the temperature has not exceeded the desired temperature.

While the present invention is disclosed by reference to the preferred embodiments and examples detailed above, it is to be understood that these examples are intended in an illustrative rather than limiting sense, as it is contemplated that modifications will readily occur to those skilled in the art, which modifications will be within the spirit of the invention and the scope of the appended claims.

What is claimed is:

1. An apparatus for ablating at least a portion of a nasal concha comprising:
    a catheter having a distal portion with a length operable for positioning through a nostril of a patient into a nasal meatus adjacent a nasal concha, the catheter further including a catheter longitudinal axis and a catheter side wall; and
    an energy delivery device coupled to the catheter distal portion including one or more energy delivering probes extendable from the catheter distal portion a sufficient distance to be inserted into an interior of the nasal concha to deliver ablative energy therein, wherein the one or more energy delivering probes are extendable from the catheter side wall in a lateral direction relative to the catheter longitudinal axis.

2. The apparatus according to claim 1 wherein the one or more energy delivering probes extend a fixed distance from the catheter distal portion.

3. The apparatus according to claim 1 wherein the distance the one or more energy delivering probes extend from the catheter distal portion can be varied.

4. The apparatus according to claim 1 wherein the one or more energy delivering probes are retractable into the catheter distal portion and extendable from the catheter distal portion.

5. The apparatus according to claim 1 wherein the energy delivery device includes at least two energy delivering probes.

6. The apparatus according to claim 1 wherein the one or more energy delivering probes deliver energy selected from the group consisting of RF, microwave, ultrasonic, pulsed laser and diffuse laser energy.

7. The apparatus according to claim 1 wherein the one or more energy delivering probes are needle electrodes for delivering RF energy.

8. The apparatus according to claim 1 wherein the one or more energy delivering probes include an optical fiber for delivering laser energy.

9. The apparatus according to claim 1 wherein the one or more energy delivering probes are antenna for delivering microwave energy.

10. The apparatus according to claim 1 wherein the one or more energy delivering probes include transducers for delivering ultrasonic energy.

11. The apparatus according to claim 1 wherein the apparatus further includes an insulator positioned adjacent at least a portion of the one or more energy delivering probes to prevent the delivery of energy therethrough.

12. The apparatus according to claim 11 wherein the insulator is movable relative to the one or more energy delivering probes.

13. The apparatus according to claim 1 wherein the apparatus includes a signal generator coupleable to an energy source for generating pulses of electromagnetic energy having a frequency between about 300 and 700 megahertz.

14. The apparatus according to claim 13, wherein the apparatus further includes a processor coupled to the signal generator for generating pulses of RF energy which provide between about 5 and about 30 watts of RF energy.

15. The apparatus according to claim 14, wherein the apparatus further includes at least one sensor coupled to the processor.

16. The apparatus according to claim 15, wherein the sensor measures a property selected from the group consisting of an amount of energy delivered by the energy delivery device, an amount of heat generated at a location, an amount of impedance generated, and a temperature at a location.

17. The apparatus according to claim 14, wherein the energy delivered to the energy delivery device is controlled by the processor in response to a measured property selected from the group consisting of an amount of energy delivered by the energy delivery device, an amount of heat generated at a location, an amount of impedance generated, and a temperature at a location.

18. The apparatus according to claim 17, wherein the apparatus includes a sensor for measuring the measured property.

19. An apparatus for ablating at least a portion of a nasal concha comprising:
    a catheter having a distal portion with a length operable for positioning through a nostril of a patient into a nasal meatus adjacent a nasal concha, the catheter further including a catheter longitudinal axis and a catheter side wall;
    an energy delivery device coupled to the catheter distal portion including one or more energy delivering probes extendable from the catheter distal portion a sufficient distance to be inserted into an interior of the nasal concha to deliver ablative energy therein, wherein the one or more energy delivering probes are extendable from the catheter side wall in a lateral direction relative to the catheter longitudinal axis; and an energy source coupled to the energy delivery device for delivering energy to the probes.

20. The apparatus according to claim 19 wherein the energy source delivers energy to the one or more energy delivering probes selected from the group consisting of RF, microwave, ultrasonic, pulsed laser and diffuses laser energy.

21. The apparatus according to claim 20 wherein the one or more energy delivering probes are needle electrodes for delivering RF energy.

22. The apparatus according to claim 20 wherein the one or more energy delivering probes include an optical fiber for delivering laser energy.

23. The apparatus according to claim 20 wherein the one or more energy delivering probes are antenna for delivering microwave energy.

24. The apparatus according to claim 20 wherein the one or more energy delivering probes include transducers for delivering ultrasonic energy.

25. The apparatus according to claim 20 wherein the apparatus includes a signal generator coupled to the energy source for generating pulses of electromagnetic energy having a frequency between about 300 and 700 megahertz.

26. The apparatus according to claim 25, wherein the apparatus further includes a processor coupled to the signal generator for generating pulses of RF energy which provide between about 5 and about 30 watts of RF energy.

* * * * *

UNITED STATES PATENT AND TRADEMARK OFFICE
CERTIFICATE OF CORRECTION

PATENT NO. : 5,827,277
DATED : October 27, 1998
INVENTOR(S) : Stuart D. Edwards

It is certified that error appears in the above-identified patent and that said Letters Patent is hereby corrected as shown below:

Title page, item 63, Related U.S. Application Data, line 1, Change "Oct. 19, 1996" to --Nov. 19, 1996--;

Title page, item 63, Related U.S. Application Data, line 2, Change "Oct. 19, 1996" to --Nov. 19, 1996--;

Title page, item 63, Related U.S. Application Data, line 3, Change "Oct. 19, 1996" to --Nov. 19, 1996--;

Title page, item 63, Related U.S. Application Data, line 7, Change "Jun. 24, 1995" to --Jun. 24, 1994--.

Signed and Sealed this

Twenty-ninth Day of February, 2000

Attest:

Q. TODD DICKINSON

*Attesting Officer*    *Commissioner of Patents and Trademarks*